United States Patent [19]

Sapienza et al.

[11] Patent Number: 4,623,634

[45] Date of Patent: Nov. 18, 1986

[54] LOW TEMPERATURE CATALYSTS FOR METHANOL PRODUCTION

[76] Inventors: Richard S. Sapienza, 1 Miller Ave., Shoreham, N.Y. 11786; William A. Slegeir, 7 Florence Rd., Hampton Bays, N.Y. 11946; Thomas E. O'Hare, 11 Geiger Pl., Huntington Station, N.Y. 11746; Devinder Mahajan, 14 Locust Ct., Selden, N.Y. 11784

[21] Appl. No.: 812,708

[22] Filed: Dec. 23, 1985

Related U.S. Application Data

[60] Division of Ser. No. 710,879, Mar. 12, 1985, abandoned, which is a continuation-in-part of Ser. No. 581,935, Feb. 21, 1984, abandoned.

[51] Int. Cl.$^4$ ............................................. B01J 31/12
[52] U.S. Cl. ..................................... 502/113; 502/161
[58] Field of Search ................................. 502/113, 161

[56] References Cited

PUBLICATIONS

Brunet et al, J. Org. Chem., 45, 1937–1950 (1980).

*Primary Examiner*—Patrick P. Garvin
*Attorney, Agent, or Firm*—Margaret C. Bogosian

[57] ABSTRACT

A catalyst and process useful at low temperatures (below about 160° C.) and preferably in the range 80°–120° C. used in the production of methanol from carbon monoxide and hydrogen is disclosed. The catalyst is used in slurry form and comprises a complex reducing agent derived from the component structure NaH—RONa—M(OAc)$_2$ where M is selected from the group consisting of Ni, Pd, and Co and R is a lower alkyl group containing 1–6 carbon atoms. This catalyst is preferably used alone but is also effective in combination with a metal carbonyl of a group VI (Mo, Cr, W) metal. The preferred catalyst precursor is Nic (where M=Ni and R=tertiary amyl). Mo(CO)$_6$ is the preferred metal carbonyl if such component is used. The catalyst is subjected to a conditioning or activating step under temperature and pressure, similar to the parameters given above, to afford the active catalyst.

4 Claims, No Drawings

LOW TEMPERATURE CATALYSTS FOR METHANOL PRODUCTION

The U.S. Government has rights in this invention pursuant to Contract Number DE-AC02-76CH00016, between the U.S. Department of Energy and Associated Universities Inc.

RELATED APPLICATIONS

This is a division of application Ser. No. 710,879 filed Mar. 12, 1985, and now abandoned, which in turn is a continuation-in-part application of application Ser. No. 581,935 filed Feb. 21, 1984, and now abandoned.

BACKGROUND OF THE INVENTION

The present application describes a low temperature catalyst and a process for the production of methanol utilizing this catalyst. This catalyst allows low temperature and low pressure use for the preparation of methanol in accordance with the equation $$CO + 2H_2 \rightarrow CH_3OH$$

The pressure and temperature parameters employed for the reaction greatly influence the results and are therefore critical. One advantage of the catalyst is that it is useful at low temperatures, up to about 160° C., with temperatures in the range of 80°–120° C. being preferred. Another advantage of the catalyst is that it can be used in slurry form.

The catalyst of the present invention consists of a complex reducing agent derived from the component structure NaH—RONa—M(OAc)$_2$ where M is selected from the group consisting of Ni, Pd, and Co and R is a lower alkyl group containing 1–6 carbon atoms. The preferred complex reducing agent is Nic, in which M=Ni and R=tertiary amyl. Nic is a known agent that has been used in the past in hydrogenation reactions to convert alkynes to alkenes [Gallois et al., *J. Org. Chem.*, 45, 1946 (1980)].

The reaction $CO + 2H_2 \rightleftharpoons CH_3OH$ is favored toward the right for the production of methanol by a combination of low temperatures and relatively high pressures. The present process uses a reaction temperature of about 160° C. or less, preferably in the range of 80°–120° C., which is known in the art as a low temperature reaction.

The reaction system is operated at about 50–1000 psi with 300 psi preferred as a starting pressure. In a continuing reaction of decreasing pressure over a span of about two hours, initial pressure of 300 psi was utilized and a final pressure of 50 psi was achieved. The reactor is of the stirred or agitated type and is flushed with hydrogen prior to use and the catalysts are prepared and charged under an inert blanket, such as argon.

DETAILED DESCRIPTION OF THE INVENTION

The present invention consists of a new series of low temperature, high activity catalysts for the synthesis of methanol from carbon monoxide and hydrogen. These catalysts are capable of activating hydrogen for reducing carbonyl bonds, and are thus "hydridic" hydrogenating agents. In one embodiment of the invention, a complex reducing agent of the type NaH—RONa—M(OAc)$_2$ where M is selected from the group consisting of Ni, Pd, and Co and R is a lower alkyl group having 1–6 carbon atoms is used in a slurry reactor. The preferred complex reducing agent is where M=Ni and the utilization of Ni(OAc)$_2$ is in combination with the sodium alcoholate which is derived from tertiary amyl alcohol. This complex reducing agent is known as Nic.

In the complex reducing agent, when M=Ni and where tertiary amyl alcohol is used, the R in the complex is predominantly tertiary amyl. Thus, the preferred form of this complex reducing agent which is a precursor to the active form of the catalyst is theoretically a structured form of nickel, which contains sodium t-amyl alcoholate residues. This catalyst thus uses a Group I metal (Na) with a preferred Group VIII metal (Ni).

In another embodiment of the present invention, the catalyst consisting of the complex reducing agent of the formula NaH—ROH—M(OAc)$_2$ where M is selected from the group consisting of Ni, Pd, and Co and R is a lower alkyl group containing 1–6 carbon atoms can be incorporated into a system where the second component in the system consists of a metal carbonyl selected from the group VI metals (Cr, Mo, W), with Mo(CO)$_6$ being preferred. This catalyst system operates within the same temperature and pressure ranges as discussed above to convert CO and H$_2$ to methanol. This system not only contains the catalyst capable of activating hydrogen for reducing carbonyl bonds, it also contains a second catalyst, such as molybdenum carbonyl, capable of activating carbon monoxide.

PREPARATION OF THE CATALYST SYSTEM

The complex reducing agent catalyst was prepared from a stirred suspension of NaH added to dry nickel acetate under an inert atmosphere, such as argon, together with tert-amyl alcohol in tetrahydrofuran and an excess of tertiary amyl alcohol was added to neutralize any excess NaH. A non-pyrophoric black suspension formed and was charged into a stirred pressure reactor under argon. If this catalyst is to be used together with a metal carbonyl, the metal carbonyl is added to the reactor at this time in a solvent (usually tetrahydrofuran).

SYNTHESIS OF METHANOL

After addition of the catalyst or the catalyst/metal carbonyl system in catalytic amounts to the pressure reactor, said reactor was flushed with hydrogen and the gas mixture (2H$_2$:1CO) was added under a pressure of about 300 psi. In the stirred reactor, the pressure decreased to about 50 psi and at that point the reactor was recharged twice. In a separate run in a continuous variation, the gas mix (2H$_2$:1CO) was charged at 300 psi. Gas consumption at up to 8 psi per minute was observed. In one experiment, a yield of 2000% based on stoichiometric conversion of the complex reducing agent was achieved, with 96% selectivity for methanol and about 4% methyl formate being produced. The reaction rate was about $10^{-2}$ turnovers per second (turnovers are here defined as molecules of methanol per molecule of catalyst per second).

It is believed that the success of the present catalyst can be explained by the proposition that the metal catalyzed reactions of synthesis gas (syngas) proceed via chemisorbed carbon monoxide reacting with hydrogen to yield an oxygen coordinated species as shown in the following reaction sequence.

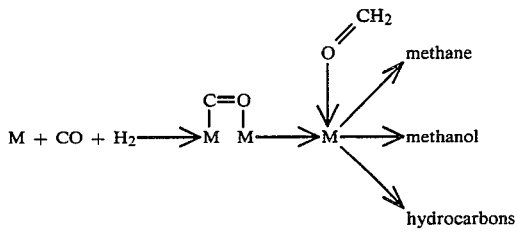

This oxymethylene intermediate can be hydrogenated to methane or can undergo chain growth by reaction with similar species. Hydrogenation may also occur across the C=O bond, cleaving the M—O bond and this accounts for the presence of oxygenated products.

Utilization of the present catalyst gave unusual yields of greater than 80% conversion to methanol in a one pass process. When the catalyst/metal carbonyl system was employed, the yields were between 30-35% conversion of methanol in a one pass process. Using the catalyst alone or in combination with the metal carbonyl, the process produces a minimum of byproducts and, for example, in a typical run gave 96% methanol based on syngas consumed.

In this specification and claims, a heavy metal salt refers to a Group VIII heavy metal, especially Ni, Co, and Pd.

The following examples are presented to further describe the invention.

EXAMPLE 1

This example illustrates the preparation, conditioning and use of the catalyst of the present invention at 100° C. and 750 psi in a batch reactor. To a stirred suspension of sodium hydride (60 mmols), and dry nickel acetate (10 mmols) in 25 ml tetrahydrofuran was added dropwise, at 45° C. and under an argon atmosphere, a solution of tertiary amyl alcohol (20 mmols) in 5 ml tetrahydrofuran. Stirring was continued for 2 hrs. during which time the liquid became black. An additional portion of tertiary amyl alcohol (32 mmol) was then added to neutralize the remaining sodium hydride, and the mixture was allowed to return to room temperature. A non-pyrophoric black suspension resulted which was then transferred under argon to a Parr Model 4561 300 ml stirred pressure reactor to which an additional 70 ml tetrahydrofuran was added. After flushing with hydrogen, the reactor was charged with 750 psi of a mixture of 33% carbon monoxide in hydrogen and heated to 100° C. The pressure decreased during the run due to syngas consumption. During this time the catalyst precursor was "conditioned", that is, converted to the active catalyst. After 1 hr, the pressure had decreased to 180 psi and the reactor was cooled. It was then recharged with syngas to 750 psi, heated again to 100° C. and similar gas consumption was observed. The reactor was cooled and a sample was withdrawn and analyzed. The total gas charge was 920 mmol with a total pressure drop equivalent to 755 mmol gas usage. Gas chromatographic analysis of the liquid showed 185 mmol methanol was produced. No methane or carbon dioxide was found in the gas phase. This amounts to about 74% yield overall based on consumed syngas, with much of the other consumption associated with conditioning.

EXAMPLE 2

This example illustrates the importance of base to the catalyst system reaction. The precursor described in Example 1 was loaded into the reactor, charged with 750 psi syngas and brought to 100° C. After about 500 psi syngas had been consumed, the reactor was drained of 70 ml of its liquid contents, leaving the solid plus about 30 ml of liquid. The same volume of THF (70 ml) was added and the reactor was recharged with 750 psi 33% carbon monoxide with hydrogen. After 3½ hours at 100° C., the pressure had decreased to 515 psi. To this system the reaction product of 1.2 g sodium hydride and 5 ml tertiary amyl alcohol was added and the reactor was recharged to 750 psi of the syngas mixture. After 2.85 hours the pressure was down to 160 psi. The total gas charge was 880 mmol with a total pressure drop equivalent to 560 mmol gas usage. Gas chromatography showed 215 mmol of methanol was produced, including some of the methanol produced in the first charging. No methane or carbon dioxide was found in the gas phase.

EXAMPLE 3

This example illustrates lower temperatures as in Example 1 are preferred. The catalyst precursor preparation and loading described in Example 1 was repeated and the reactor was charged with 750 psi 33% carbon monoxide in hydrogen. After 1.5 hours at 150° C. the pressure was down to 310 psi. With continued heating, no further pressure drop was observed. The reactor was recharged with 300 psi of the syngas mixture. After 1.2 hours at 100° C. the reaction had not proceeded and the final pressure was 380 psi. The reactor was cooled and gas and liquid samples were withdrawn. The total gas charge was 362 mmol with a pressure drop equivalent to 86 mmol. Gas chromatography showed 20 mmol of methanol was produced.

EXAMPLE 4

This example shows this catalyst used at 120° C. The catalyst precursor described in Example 1 was subjected to gas feed of 300 psi syngas (2H$_2$:CO). After 1 hr at 120° C. the pressure had decreased to 180 psi. The reactor was recharged three more times with 300 psi and run at 120° C. with similar results. The reaction was cooled and a sample was withdrawn and analyzed. The total gas charge was 740 mmol with a total pressure drop equivalent to 570 mmol gas usage. Gas chromatography showed 160 mmol of methanol was produced.

EXAMPLE 5

This example demonstrates the catalyst used at 80° C. The catalyst precursor described in Example 1 was subjected to 300 psi 33% carbon monoxide with hydrogen. After 3.4 hours at 80° C. the pressure was down to 120 psi. The reactor was recharged with 300 psi of the syngas mixture. After 1.3 hrs at 80° C. the pressure had dropped to 140 psi. The reactor was cooled and a sample withdrawn and analyzed. The total gas charge was 360 mmol with a pressure drop equivalent to 255 mmol gas usage. Gas chromatography showed 82 mmol methanol was produced.

EXAMPLE 6

This example demonstrates the catalyst conditioned at 100° C., then used at 150° C. The catalyst precursor described in Example 1 was subjected to 300 psi 33% carbon monoxide with hydrogen. After 2.5 hours at 100° C. the pressure was down to 130 psi. The reactor was recharged with 300 psi of the syngas mixture. After 1 hour at 150° C. the pressure was down to 210 psi. The reactor was cooled and a sample was withdrawn and analyzed. Gas chromatography showed 54 mmol methanol produced.

EXAMPLE 7

This example shows that the catalyst may be reused. The catalyst precursor described in Example 1 was subjected to gas feed at 300 psi 2:1 synthesis gas (2H$_2$:CO). After 43 min. at 100° C. the pressure was down to 180 psi. The reactor was recharged with 300 psi of the syngas mixture. After 54 min. at 120° C. the pressure was down to 160 psi. The reactor was recharged two more times under similar conditions. The third charge was at 120° C. for 21 min., allowing the pressure to drop to 180 psi. The fourth charge dropped to 120 psi while at 120° C. for 45 min. The reactor was cooled and a sample withdrawn and analyzed. Approximately 5.8 g of syngas was consumed, with analysis indicating 5.0 g methanol had been formed, with no significant amounts of other organic compounds found. The excess gas consumption appears to be due to inorganic side reactions, some of which are related to conditioning.

EXAMPLE 8

This example demonstrates conditioning at 100° C. and use at 80° C. The catalyst precursor described in Example 1 was subjected to gas feed of 300 psi 33% carbon monoxide with hydrogen. After 90 min. at 100° C. the pressure was down to 170 psi. The reactor was recharged with 300 psi of the syngas. After 60 min. at 80° C. the pressure was down to 180 psi. The reactor was recharged again in a similar manner with the same results. The reactor was cooled and a sample withdrawn and analyzed. The total gas charge was 550 mmol with a pressure drop equivalent to 306 mmol gas usage, affording 2.6 g methanol.

EXAMPLE 9

This example illustrates the preparation, conditioning and use of the catalyst/metal carbonyl system at 100° C. and 300 psi in a batch reactor.

To a stirred suspension of sodium hydride (60 mmols), and dry nickel acetate (10 mmols) in 25 ml tetrahydrofuran was added dropwise, at 45° C. and under an argon atmosphere, a solution of tertiary amyl alcohol (20 mmols) in 5 ml tetrahydrofuran. Stirring was continued for 2 hrs. during which time the liquid became black. An additional portion of tertiary amyl alcohol (32 mmol) was then added to neutralize the remaining sodium hydride, and the mixture was allowed to return to room temperature.

A non-pyrophoric black suspension resulted which was then transferred under argon to a Parr Model 4561 300 ml stirred pressure reactor containing 1.3 g molybdenum hexacarbonyl (5 mmol), to which an additional 70 ml tetrahydrofuran was added. After flushing with hydrogen, the reactor was charged with 300 psi of a mixture of 33% carbon monoxide in hydrogen and heated to 100° C. The pressure decreased during the run due to syngas consumption. During this time the catalyst precursor was "conditioned," that is, converted to the active catalyst. After 2 hr, the pressure had decreased to 50 psi and the reactor was cooled. It was then recharged with syngas to 300 psi, heated again to 100° C. and similar gas consumption was observed. After a third charging and heating cycle, the reactor was cooled and a sample was withdrawn and analyzed.

The total gas charge was 300 mmol with a total pressure drop equivalent to 270 mmol gas usage. Gas chromatographic analysis of the liquid showed 67 mmol methanol was produced. No methane or carbon dioxide was found in the gas phase. This amounts to about 74% yield overall based on consumed syngas, with much of the other gas consumption (CO) associated with conditioning.

EXAMPLE 10

The catalyst system described in Example 9 was subjected to gas feed of 300 psi 33% carbon monoxide with hydrogen doped with 1670 ppm of hydrogen sulfide. After 2 hours at 100° C., the system was recharged with this same mixture. Analysis after 2 additional hours of reaction showed 45 mmol methanol which corresponds to a yield of about 33%.

EXAMPLE 11

The catalyst system described in Example 9 with chromium hexacarbonyl substituted for molybdenum hexacarbonyl gave similar gas consumption as shown in Example 9 at 150° C.

EXAMPLE 12

The catalyst system described in Example 9 with cobalt acetate substituted for nickel acetate after 14 hours at 125° C. gave 11% conversion to methanol with a single charge of 300 psi syngas containing 33% CO.

We claim:

1. A catalyst used in the synthesis of methanol from carbon monoxide and hydrogen which comprises catalytic amounts in slurry form of a complex reducing agent of the type NaH—ROH—M(OAc)$_2$ wherein M is selected from the group consisting of Ni, Pd, and Co and R is a lower alkyl group containing from 1-6 carbon atoms, combined with a group VI metal carbonyl.

2. The catalyst of claim 1 wherein the complex reducing agent is derived from NaH—ROH—Ni(OAc)$_2$.

3. The catalyst of claim 2 wherein R is tertiary amyl.

4. The catalyst of claim 1 wherein the metal carbonyl is molybdenum hexacarbonyl.

* * * * *